United States Patent [19]

Nelson et al.

[11] 4,015,602
[45] Apr. 5, 1977

[54] EAR MOLD INJECTION DISPENSER

[75] Inventors: Eugene A. Nelson; Woodrow R. Rice, both of Wichita, Kans.

[73] Assignee: Mid-States Laboratories, Inc., Wichita, Kans.

[22] Filed: Dec. 8, 1975

[21] Appl. No.: 638,449

[52] U.S. Cl. .............................. 128/234; 128/239; 222/561

[51] Int. Cl.² .......................................... A61M 1/00

[58] Field of Search ............... 128/234, 218 R, 2 R, 128/215, 216, 239; 222/561, 567

[56] References Cited

UNITED STATES PATENTS

| 904,745 | 11/1908 | Adams | 222/561 |
|---|---|---|---|
| 1,119,033 | 12/1914 | Paddock | 222/561 X |
| 2,842,127 | 7/1958 | Everett | 128/218 R |
| 2,969,167 | 1/1961 | Libit | 222/561 X |
| 3,316,909 | 5/1967 | Cowley | 128/234 X |
| 3,648,695 | 3/1972 | Bowen | 128/239 X |
| 3,884,231 | 5/1975 | Peters | 128/239 X |

Primary Examiner—John D. Yasko
Attorney, Agent, or Firm—John H. Widdowson; Edwin H. Crabtree

[57] ABSTRACT

An ear mold injection dispenser for dispensing impression material into an ear canal and a cavity of the ear. The dispenser includes a tubular body having a valve. The impression material is mixed inside the tubular body. A plunger is inserted into the tubular body and the valve is open. The plunger pushes the material through the valve into a funnel which is inserted into the ear. The funnel is detachable from the tubular body so that the correct size of funnel can be selected for inserting inside the ear canal.

6 Claims, 9 Drawing Figures

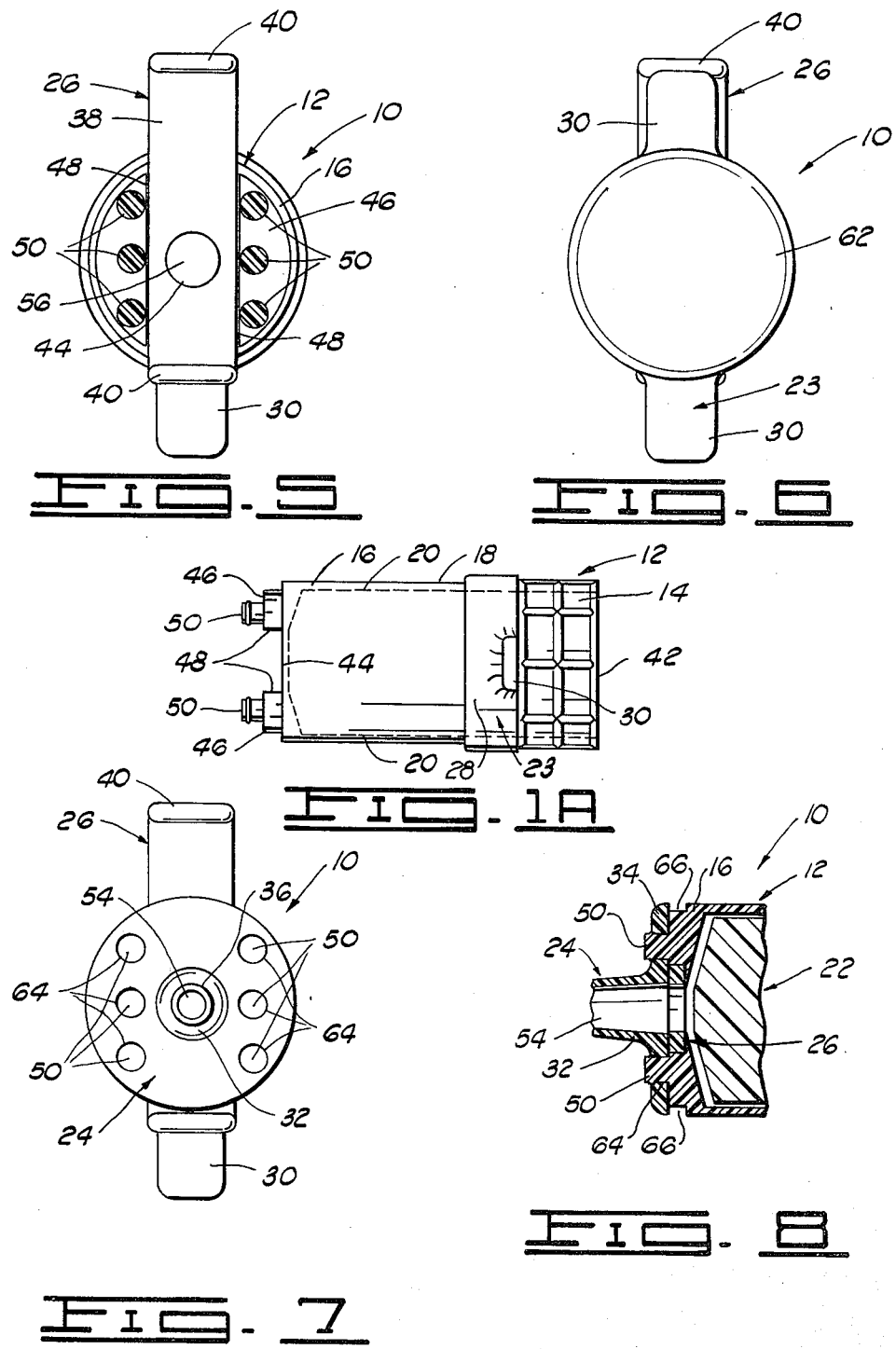

EAR MOLD INJECTION DISPENSER

BACKGROUND OF THE INVENTION

This invention relates generally to a syringe, dispenser, or the like and more particularly but not by way of limitation to a dispenser for injecting impression material inside an ear canal and an ear cavity.

Heretofore in the casting of an ear mold the impression material is mixed separately and poured into a dispenser for injecting into the ear. This method is time consuming and the impression material is often wasted during the process. Also the dispenser and the mixing apparatus each have to be cleaned separately.

There are many types of syringes, injection apparatuses and dispensing devices used with different types of valves. None of the prior art devices disclose the novel dispenser for injecting impression material in an ear as herein described.

SUMMARY OF THE INVENTION

The subject invention provides a dispenser wherein the impression material can be mixed inside the dispenser eliminating the need of having to separately mix the material.

The dispenser includes a valve for closing the dispenser when the material is mixed. The valve is open when it is desired to inject the impression material into the ear. Also the valve can be used to control the flow of the material through the dispenser.

The dispenser also includes interchangeable funnels having different size end portions. The end portion of the funnel is inserted into the ear canal.

The dispenser is made of a transparent plastic or the like. The various elements of the dispenser can be quickly detached from each other for ease in cleaning and assembling. Also because of the dispensers novel structure any worn parts can easily be replaced.

The ear mold injection dispenser includes a tubular body. Surrounding the outer circumference of the tubular body is a grip for holding the dispenser when in use. A sliding plunger is inserted into the tubular body after the impression material is mixed in the body. A valve is mounted in the tubular body for controlling the flow of the material from the dispenser. A funnel is attached to the tubular body and receives the impression material from the tubular body through the valve and injects the material into the ear canal and the ear cavity.

The advantages and objects of the invention will become evident from the following detailed description when read in conjunction with the accompanying drawings which illustrate the preferred embodiments of the invention.

BRIEF DESCRIPTION OF THE DRAWINGS

FIG. 1a is a side view of the tubular body.

FIG. 5 is a sectional front view taken along lines 5—5 shown in FIG. 2.

FIG. 6 is a rear view of the dispenser.

FIG. 7 is a front view of the dispenser.

FIG. 8 is a sectional view taken along lines 8—8 shown in FIG. 2.

DETAILED DESCRIPTION OF THE DRAWINGS

Figure 1:
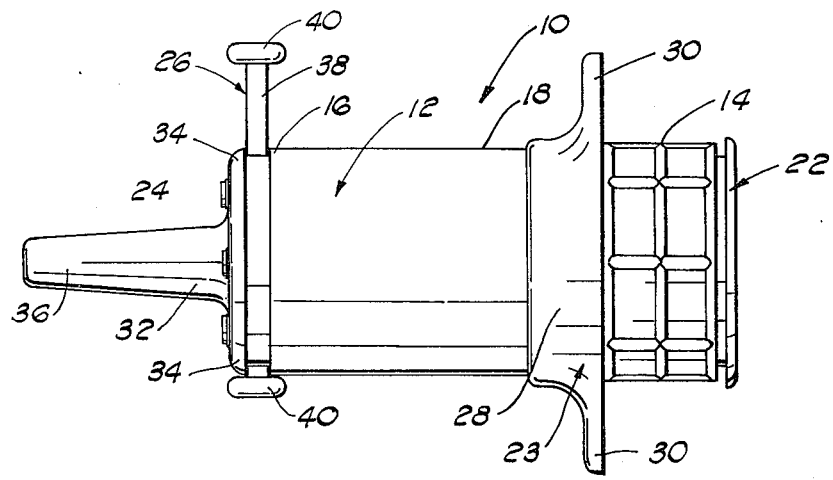
FIG. 1 is a side view of the ear mold injection dispenser.

In FIG. 1 the ear mold injection dispenser is designated by general reference numeral 10. The dispenser 10 includes a tubular body 12 having a first end portion 14, a second end portion 16, outer circumference 18 and an inner circumference 20 which is shown in FIG. 1a. The dispenser 10 further includes a cylindrical plunger 22 inserted inside the inner circumference 20 of the body 12, a grip 23 attached around the outer circumference 18 of the body 12, a funnel 24 attached to the second end portion 16 of the body 12, and a valve 26 mounted between the funnel 24 and the body 12.

The grip 23 includes a ring 28 slidably mounted around the outer circumference 18 of the body 12 and disposed adjacent the first end portion 14 of the body 12. The grip 23 further includes outwardly extending handles 30 integrally attached to the ring 28 for holding the dispenser 10.

The funnel 24 includes a first end portion 32 having an annular flange 34 integrally formed therearound which is attached to the second end portion 16 of the body 12. The funnel 24 is tapered inwardly from the first end portion 32 toward a second end portion 36. The second end portion 36 of the funnel 24 is rounded for inserting into the ear canal.

The valve 26 includes a rectangular shaped slide member 38 which is mounted between the first end portion 32 of the funnel 24 and the second end portion 16 of the body 12. The valve 26 further includes stops 40 attached at both ends of the slide member 38.

In FIG. 1a a side view of the tubular body 12 is shown rotated at an angle 90° from the position of the dispenser 10 shown in FIG. 1. In this view the funnel 24, valve 26 and plunger 22 have been removed from the body 12.

Shown in dotted lines in this view is the inner circumference 20 of the tube 12. The first end portion 14 of the body 12 includes an opening 42 for receiving the plunger 22 therein. The second end portion 16 of the body 12 includes a smaller opening 44 for discharging the impression material therethrough.

A front 46 of the second end portion 16 includes a slot 48 for slidably receiving the slide member 38 of the valve 26. Integrally attached to the front 46 of the first end portion 16 are outwardly extending posts 50 which are used to engage the flange portion 34 of the funnel 24.

Figure 2:
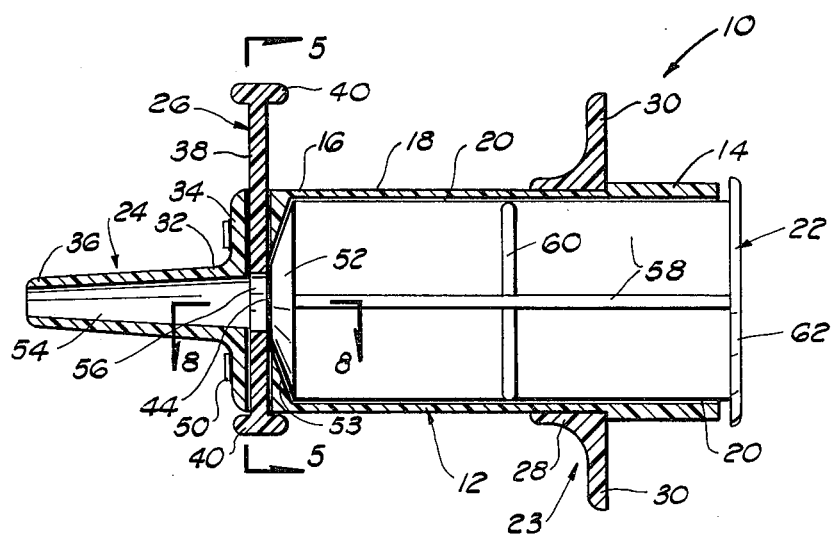
FIG. 2 is a sectional side view of the dispenser taken through the center of the dispenser.

In FIG. 2 a sectional side view is taken through the center of the body 12, valve 26, and funnel 24 as shown in FIG. 1. The plunger 22 is shown received inside the inner circumference 20 of the body 12. The plunger 22 includes a convex annular first end porion 52 which is disposed adjacent a concave surface 53 and the opening 44 of the second end portion 16 of the body 12. A tapered opening 54 can be seen extending through the funnel 24. In this view the valve 26 is in an open position so that an aperture 56 in the slide member 38 of the valve 26 is aligned with the opening 44 of the body 12 and the tapered opening 54 of the funnel 24.

Figures 3, 4:
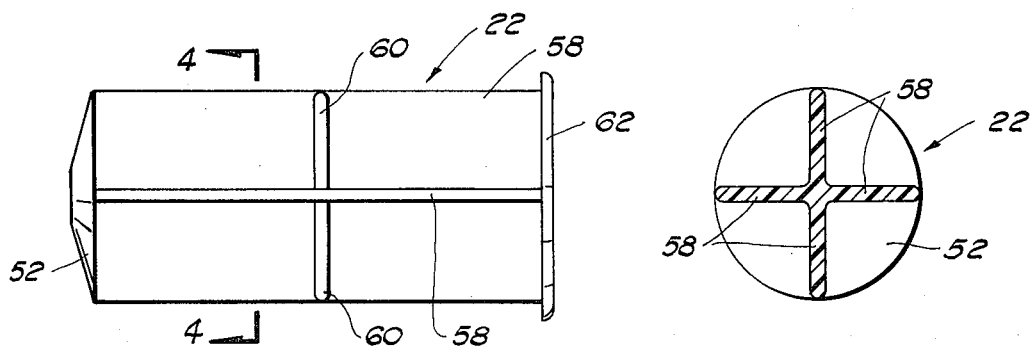
FIG. 3 is a side view of the plunger.
FIG. 4 is a sectional front view of the plunger taken along lines 4—4 shown in FIG. 3.

In FIG. 3 a side view of the plunger 22 is seen. The plunger 22 includes the convex annular first end portion 52, elongated intersecting support members 58, an annular center brace 60 and an annular second end portion 62. The annular second end portion 62 is used to push the plunger 22 through the inner circumference 20 of the body 12. It should be noted in FIG. 2 that the edges of the support members 58 are adjacent the inner circumference 20 of the body 12 and are used as guides to keep the plunger 22 in alignment as it is received inside the body 12.

FIG. 4 is a cross section of the plunger 22 taken along lines 4—4 shown in FIG. 3. In this view the intersecting support members 58 can be seen attached to the rear of the convex first end portion 52.

FIG. 5 is a front view of the dispenser 10 taken along lines 5—5 shown in FIG. 2. In this view the rectangular shaped slide member 38 of the valve 26 can be seen received inside the slot 48 in the front 46 of the second end portion 16 of the body 12. Shown in cross section are the posts 50 attached to the front 46 of the second end portion 16.

By sliding the valve 26 upward the lower stop 40 of the valve 26 contacts the side of the first end portion 16 of the body 12. At this position the aperture 56 in the valve 26 is aligned with the opening 44 of the first end portion 16 of the body 12.

FIG. 6 is a rear view of the dispenser 10. In this view the annular second end portion 62 can be seen with the handles 30 of the grip 23 and a portion of the valve 26 with the stop 40.

In FIG. 7 a front view of the dispenser 10 is shown. In this view the funnel 24 can be seen with the flange 34 having apertures 64 for receiving the outwardly extending posts 50 of the first end portion 16 of the body 12. Also seen in this view is the tapered opening 54 of the funnel 24 extending from the first end portion 32 inwardly toward the second end portion 36.

In FIG. 8 a sectional portion of the dispenser 10 is shown taken along lines 8—8 shown in FIG. 2. In this view the apertures 64 in the flange 34 of the funnel 24 are shown receiving the outwardly extending posts 50 of the second end portion 16 of the body 12. The funnel 24 is quickly detachable from the body 12 by inserting the edge of a coin, screw driver, or the like inside a slot 66 in the side of the second end portion 16. By inserting a coin inside the slott 66 and urging the flange portion 34 outwardly away from the second end portion 16, the outwardly extending post 50 are released from the apertures 64 in the funnel 34. The funnel 34 is removed and a funnel having either a larger or smaller second end portion 36 is reattached to the body 12 for fitting into a different size ear canal.

In operation the dispenser 10 is used by first removing the plunger 22 from the body 12. The valve 26 is then closed. The inside of the body 12 is now used for mixing the impression material. The impression material may be in a powder of liquid form and is mixed with a catalyst. The impression material may be ethyl methacrylate or any other similar type of chemical compound used for making ear impressions. When the impression material is mixed, the plunger 22 is inserted into the opening 42 and received inside the inner circumference 20 of the body 12. The valve 26 is now opened. The convex annular first end portion 52 contacts the impression material in the body 12 and urges the material through the aperture 56 in the valve 26 and into the tapered opening 54 of the funnel 24.

In the meantime the funnel 24 has been inserted into the ear canal. As the plunger 22 is urged into the body 12, the impression material is discharged through the funnel 24 and received inside the ear canal. As the ear canal is filled, the dispenser 10 is removed from the ear canal and the impression material is now discharged into the ear cavity. When all of the impression material has been discharged from the dispenser 10 it is removed from the ear. The dispenser 10 can now be quickly cleaned by removing the plunger 22 and detaching the funnel 24 and the valve 26 from the tubular body 12.

Changes may be made in the construction and arrangement of the parts or elements of the embodiments as disclosed herein without departing from the spirit or scope of the invention as defined in the following claims.

I claim:

1. An ear mold injection dispenser for receiving and mixing ear impression material therein and dispensing the material into the ear canal and the cavity of the ear, the dispenser comprising:

a tubular body having an opening in a first end portion of said body, an opening in a second end portion of said body, said body having an outer circumference and an inner circumference, the front of the second end portion of said body including outwardly extending posts integrally formed therein;

a sliding plunger received in the opening of the first end portion of said body, the sides of said plunger disposed adjacent the inner circumference of said body;

a funnel having a first end portion and a second end portion, the first end portion of said funnel including a flange portion therearound, said flange portion having apertures therethrough for receiving said posts therein in a snap fit; and a valve slidably mounted between the first end portion of said funnel and the second end portion of said body.

2. The dispenser as described in claim 1 further including, an annular shaped grip slidably mounted around the outer circumference of said body, said grip having outwardly extending handles for holding the dispenser when dispensing the impression material into the ear.

3. The dispenser as described in claim 1 wherein, said sliding plunger comprises:

elongated intersecting support members, the edges of the support members disposed adjacent the inner circumference of said body when said plunger is received therein;

a convex annular shaped first end portion attached at one end of the support members, the convex annular shaped first end portion contacting the impression material inside said body and dispensing the material through the opening in the second end portion of said body; and an annular shaped second end portion attached to the other end of the support members, the second end portion used to push said plunger through the inner circumference of said body.

4. The dispenser as described in claim 1 wherein, said valve is rectangular in shape having an aperture therein, said valve received in a slot in the second end portion of said body, the ends of said valve extending outwardly from said body for moving said valve in the slot so that the aperture of said valve can be aligned with the opening of the second end portion of said body for dispensing the impression material into the ear.

5. The dispenser as described in claim 1 wherein, said funnel is tapered inwardly from the first end portion to the second end portion, the second end portion rounded at the ends thereof for inserting into the ear canal.

6. The dispenser as described in claim 5 wherein, said funnel is detachable from said body for attaching a selected funnel having a different size second end portion for inserting into a different size ear canal.

* * * * *